United States Patent [19]

Shimizu et al.

[11] Patent Number: 4,537,774

[45] Date of Patent: Aug. 27, 1985

[54] HOT-WATER EXTRACTS OF NEEM BARK

[75] Inventors: Masaki Shimizu, Tokyo; Tadashi Sudo, Honmachi; Takeo Nomura, Hino, all of Japan

[73] Assignee: Terumo Corporation, Tokyo, Japan

[21] Appl. No.: 541,479

[22] Filed: Oct. 13, 1983

Related U.S. Application Data

[63] Continuation of Ser. No. 290,876, Aug. 7, 1981, abandoned.

[30] Foreign Application Priority Data

Aug. 19, 1980 [JP] Japan ................................ 55-113786
Sep. 8, 1980 [JP] Japan ................................ 55-124353
Apr. 24, 1981 [JP] Japan ................................ 56-61482
Apr. 24, 1981 [JP] Japan ................................ 56-61483

[51] Int. Cl.$^3$ ............................................ A61K 35/78
[52] U.S. Cl. ................................................ 424/195.1
[58] Field of Search .......................................... 424/195

[56] References Cited

FOREIGN PATENT DOCUMENTS 10124 4/1978 Japan .................................... 424/195
13689 5/1978 Japan .................................... 424/195

OTHER PUBLICATIONS

Cancer Research, 27:6-8, 11 and 105, 1967.
Tetrahedron, 10:45-54, 1960, Pergaman Press Ltd., Ireland.

Primary Examiner—Albert T. Meyers
Assistant Examiner—John W. Rollins
Attorney, Agent, or Firm—Frishauf, Holtz, Goodman & Woodward

[57] ABSTRACT

Hot-water extracts of the neem bark produced by treating the bark of neem with water at a temperature from 0° to 40° C. and subjecting the residue from said pre-extraction treatment to extraction treatment with hot water. Purification of the extract thus produced by means of alcohol precipitation or dialysis gives products of a higher purity. Moreover, treatments prior to the pre-extraction treatment with water at 0°-40° C. with a non-polar organic solvent having a dielectric constant of 10 or lower and a polar organic solvent having a dielectric constant from 15 to 35 yields neem extracts of a further higher purity. The hot-water extracts of the neem bark according to the present invention possess activity against mouse L-5178Y cells and transplanted sarcoma 180 tumors.

16 Claims, 5 Drawing Figures

HOT-WATER EXTRACTS OF NEEM BARK

This application is a continuation of application Ser. No. 290,876, filed Aug. 7, 1981, now abandoned.

BACKGROUND OF THE INVENTION

1. Field of the Invention

This invention relates to novel hot-water extracts of the neem bark. The hot-water extracts of the neem bark according to the invention possess activity against mouse L-5178Y cells and transplanted sarcoma 180 tumors and antimitotic activity in sea urchin eggs.

As a result of extensive studies on pharmacological actions of constituents contained in the neem materials, it has now been found that substances possessing activity as described above are produced by treating the neem bark prior to extraction with water at a temperature from 0° to 40° C. or, prior to such treatment, treating the same with a polar organic solvent having a dielectric constant from 15 to 35 and a non-polar organic solvent having a dielectric constant of 10 or lower and then subjecting the residue from the pretreatment to extraction with hot water, and that the pharmacological activities are enhanced by purifying the resulting extract by means of precipitation with an alcohol or by dialysis.

It is therefore the object of the present invention to provide hot-water extracts of the neem bark possessing activity against mouse L-5178Y cells and transplanted sarcoma 180 tumors.

2. Description of the Prior Art

It is heretofore known that neem extracts contain various pharmacologically active constituents. In fact, there is disclosed a method of producing cosmetics for the skin from the bark, leaves, flowers, fruits, branch, root epidermis or resin of neem by extracting the same with water of a hydrophilic solvent or by finely pulverizing the same (Japanese Patent Publication Nos. 28853/77, 28854/77 and 10125/78); a method of preparing from such neem materials the constituents possessing gastrointestinal and hepatic function-improving activities by extracting the same with a hydrophilic solvent and/or hot water (Japanese Patent Publication No. 10124/78); and a method of preparing from such neem materials the constituents that are effective for the therapy of dermatological and rheumatic diseases by extracting the same with a hydrophobic solvent (Japanese Patent Publication No. 13689/78). These prior-art methods are distinct from the present invention in that there are involved in order to produce the active constituents no pretreatment but direct extraction process only.

SUMMARY OF THE INVENTION

This invention relates to hot-water extracts of the neem bark which are produced by treating neem bark prior to extraction with water at a temperature from 0° to 40° C., and subjecting the residue from the pretreatment to extraction with hot water and, if desired, purifying the hot-water extract by means of precipitation with an alcohol or by dialysis.

Furthermore, it is concerned with hot-water extracts of the neem bark which are produced by treating the neem bark prior to extraction with a polar organic solvent having a dielectric constant from 15 to 30 and, if desired, prior to such treatment, treating the same with a non-polar organic solvent having a dielectric constant of 10 or lower, then treating the residue from the pretreatment(s) with water at a temperature from 0° to 40° C., subjecting the residue from the above pretreatments to extraction with hot water and, if desired, purifying the hot-water extract by means of precipitation with an alcohol or by dialysis.

As described below, the neem extracts according to the invention exhibit antimitotic activity in fertilized eggs of the sea urchin as well as growth-inhibitory actions against mouse sarcoma 180 ascites and solid tumors and mouse L-5178Y cells.

Neem is a large tree having a height of a least 10 meters which is native in the topics and called *Melia azadirachta* as a bontanical name. Its bark is utilized in the present invention. The bark is preferably dried and finely divided for use in the invention.

According to the invention, the neem bark, prior to extraction of the active constituents, is initially treated with water at a temperature from 0° to 40° C. The treatment prior to extraction is conducted for several hours to one day in a conventional manner. Then, the residue resulting from such pretreatment is treated with hot water for extraction of the active ingredients. This step is effected either by adding hot water to the neem bark or by adding water to the neem bark followed by heating of the mixture to boiling. The heating may be carried out in a boiling water bath or by direct heating. The period of extraction time is usually from 1 to 48 hours, although it may appropriately be fixed depending upon quality of the material and other conditions. After completion of the extraction, the extraction mixture is filtered to obtain an extract. When the extract is subjected to evaporation to dryness, freeze-drying, drying with a spray dryer or the like, there is obtained the hot-water extract of the neem bark according to the present invention as brown powders.

The neem bark extract thus obtained may be used as it is, or it may be purified by means of precipitation with an alcohol or by a permeable membrane to give a neem bark extract of higher purity. the alcohol precipitation is accomplished by adding an alcohol to an aqueous solution of the neem bark extract as obtained above or to the hot-water extract. Alternatively, insoluble matter is isolated by directly treating the powdery extract as mentioned above with an aqueous alcohol.

The alcohol preferably employed is selected from methanol or ethanol, which is preferably added in such an amount that the alcohol concentration in the aqueous solution of the extract or in the extract solution is from 20 to 90%, especially about 80%. Precipitates formed in the aqueous solution are isolated by a conventional method, for example, centrifugal separation. The precipitates thus obtained are washed with an aqueous alcohol of the same concentration as above and, if desired, with a nearly 100% alcohol and subsequently with ether and then drying with flowing air or vacuum drying.

The diaphragmatic method is carried out by placing the neem extract as mentioned above or aqueous solution of said extract in a diaphragm to effect dialysis of undesired constituents. The diaphragm employed is the type through which substances of a molecular weight of 50,000 or lower can be fractionated or passed. For example, Spectra Por 1-6 (manufactured by Spectrum Medical Industries Co.) which is made of regenerated cellulose or Visking tube (manufactured by Union Carbide Company) which is made of cellulose acetate is preferably employed. Most suitable is Spectra Por 6

(fraction molecular weight 50,000). The active constituents are isolated from the internal dialyzate by a conventional method. The desired neem bark extract is obtained by concentrating the internal dialyzate to dryness or by freeze-drying the same.

In the course of extraction steps according to the invention, the neem bark prior to the pretreatment with water at 0°–40° C. may be treated with a polar organic solvent having a dielectric constant of 15–35 or, further prior to such treatment, with a non-polar organic solvent having a dielectric constant of 10 or lower to yield a neem bark extract of higher activity.

Illustrative of the polar organic solvent used in the aforementioned pretreatment are alcohols such as methanol, ethanol, propanols and n-butanol, pyridine, acetone and the like. As examples of the non-polar organic solvent are mentioned benzene, toluene, xylenes, n-hexane, chloroform, carbon tetrachloride, ethyl acetate and the like.

The above-mentioned pretreatment steps are carried out by adding a predetermined solvent to the starting neem bark.

The neem bark extracts of the present invention have the following characteristics:
(1) Appearance: Brown powders.
(2) Molecular weight: 50,000 or higher based upon the Spectra Por 6 dialysis.
(3) IR absorption spectrum: As shown in FIG. 4 (for the extract in Example 12). IR $\nu_{max}^{kBr}$ cm.$^{-1}$: ca. 3400, 1620, 1020.
(4) UV absorption spectrum: As shown in FIG. 5 (for the extract in Example 12). Water was used as the solvent. UV λmax. 274 nm.
(5) Sugar content (as determined by the phenol sulfuric acid method): 82.4% (in terms of soluble starch).

The neem bark extracts of the present invention have activity against mouse L-5178Y cells and transplanted sarcoma 180 tumors. They may be administered parenterally, for example, by subcutaneous, intravenous or intramuscular injection, or orally in the form of tablets, capsules, granules, powders, syrup or the like.

The extracts of the present invention are formulated in conventional manners. For example, dried powders of the present extract are placed in a vessel such as a vial. Separately, a physiological saline solution, aqueous glucose solution or suspension of carboxymethylcellulose (CMC) is prepared in a vessel such as an ampule. The powders are dissolved or suspended when used. Alternatively, the extract in the form of an emulsion may be injected. In the case of a water-in-oil (w/o) emulsion, for example, a combination of a mineral oil such as liquid paraffin or a vegetable oil such as sesame oil or peanut oil with a surfactant such as sorbitan aliphatic esters is employed.

DESCRIPTION OF THE PREFERRED EMBODIMENTS

Figure 1:
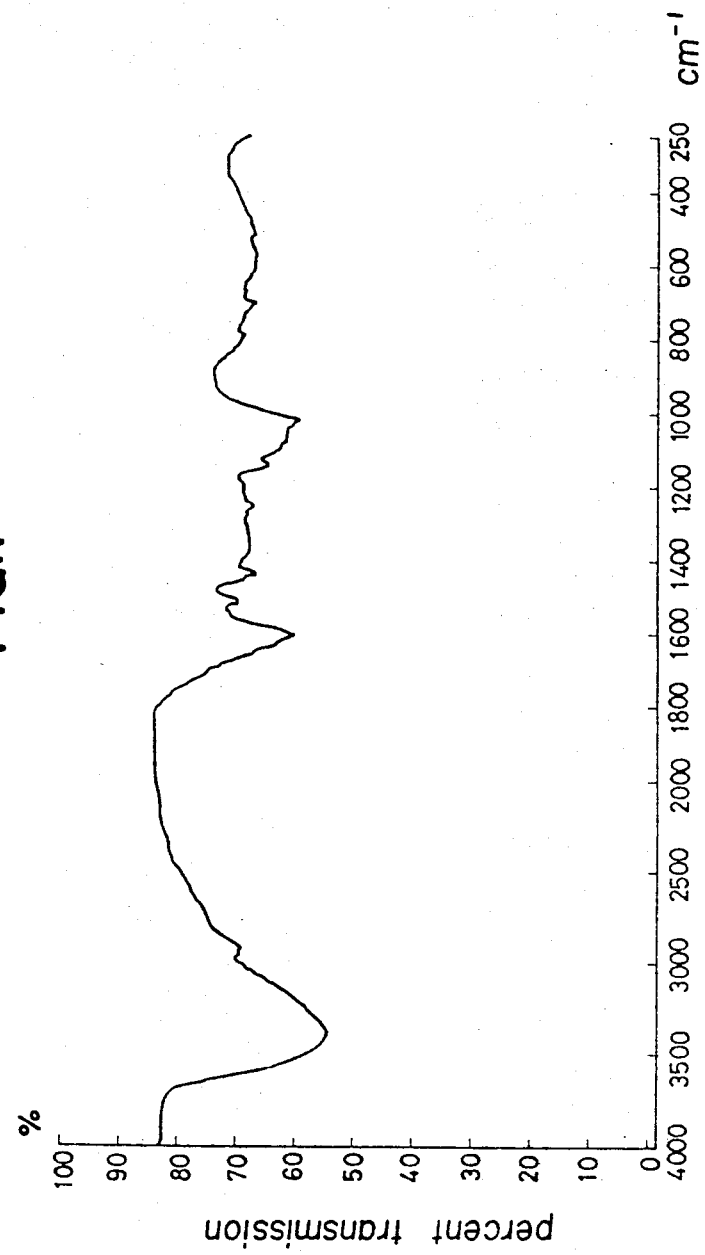
FIGS. 1, 2 and 4 show IR absorption spectra of the hot-water extracts of the neem bark obtained in Examples 1, 6 and 12, respectively.
Figure 2:
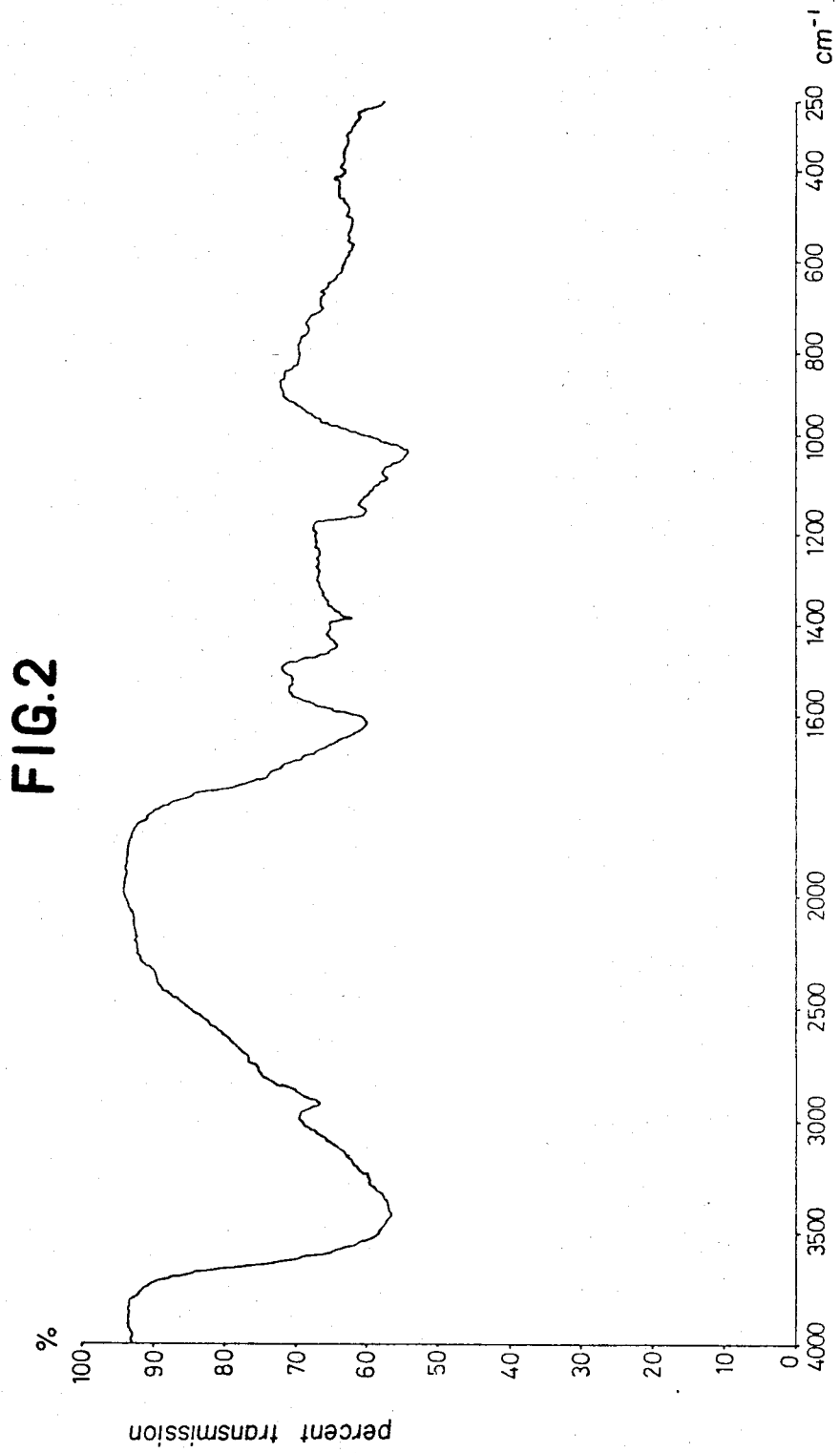
Figure 3:
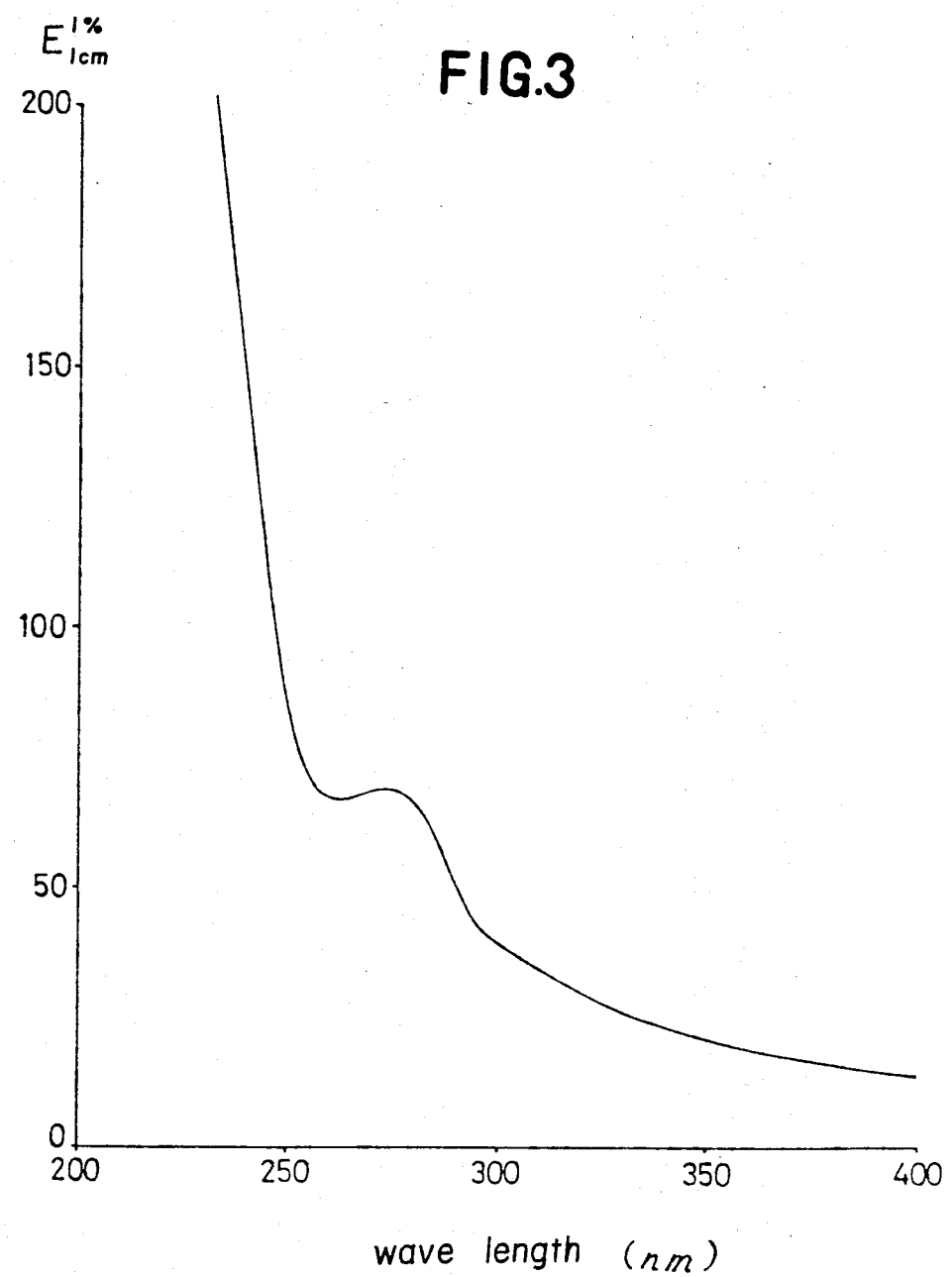
FIGS. 3 and 5 show UV absorption spectra of the hot-water extracts of the neem bark obtained in Examples 6 and 12, respectively.
Figure 4:
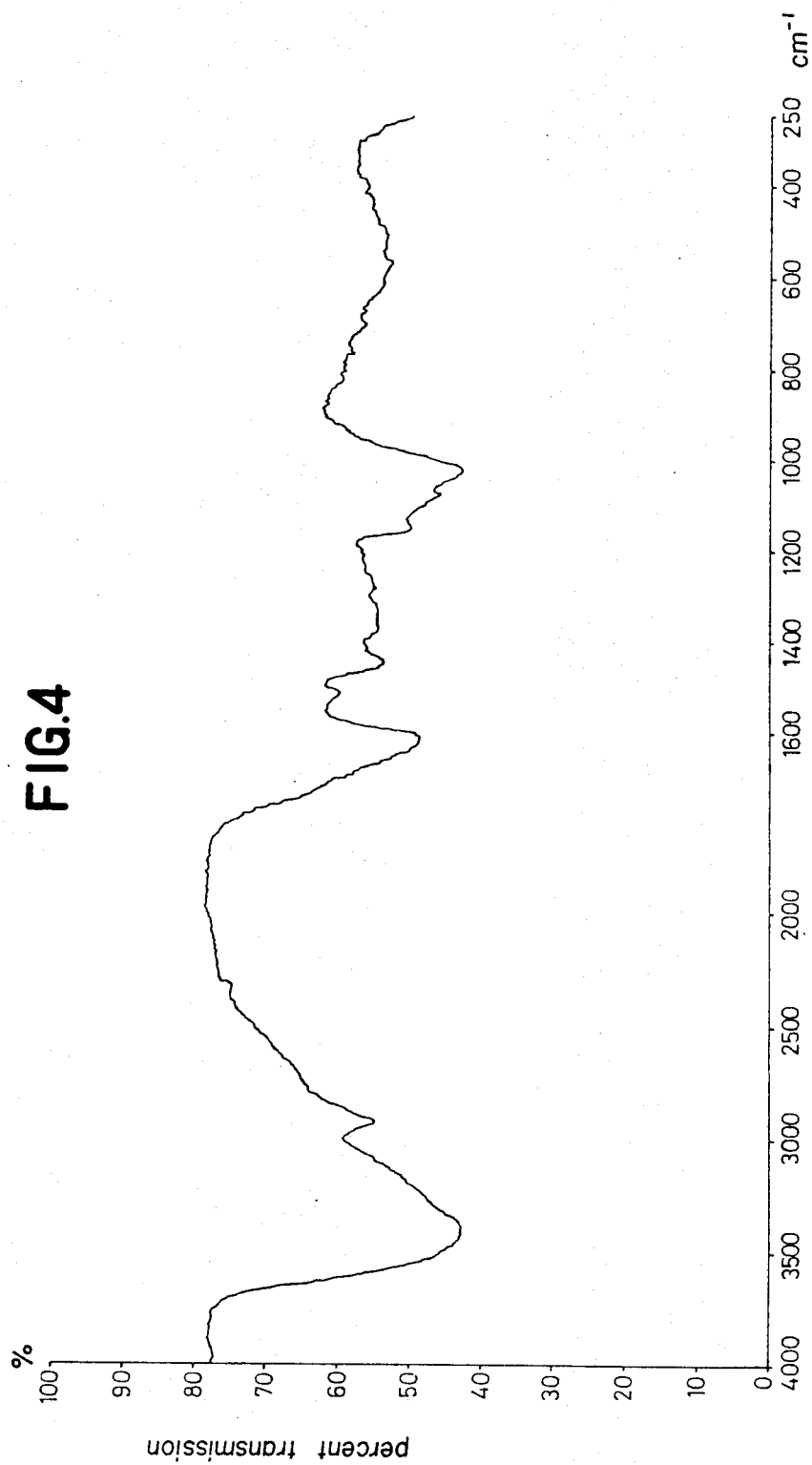
Figure 5:
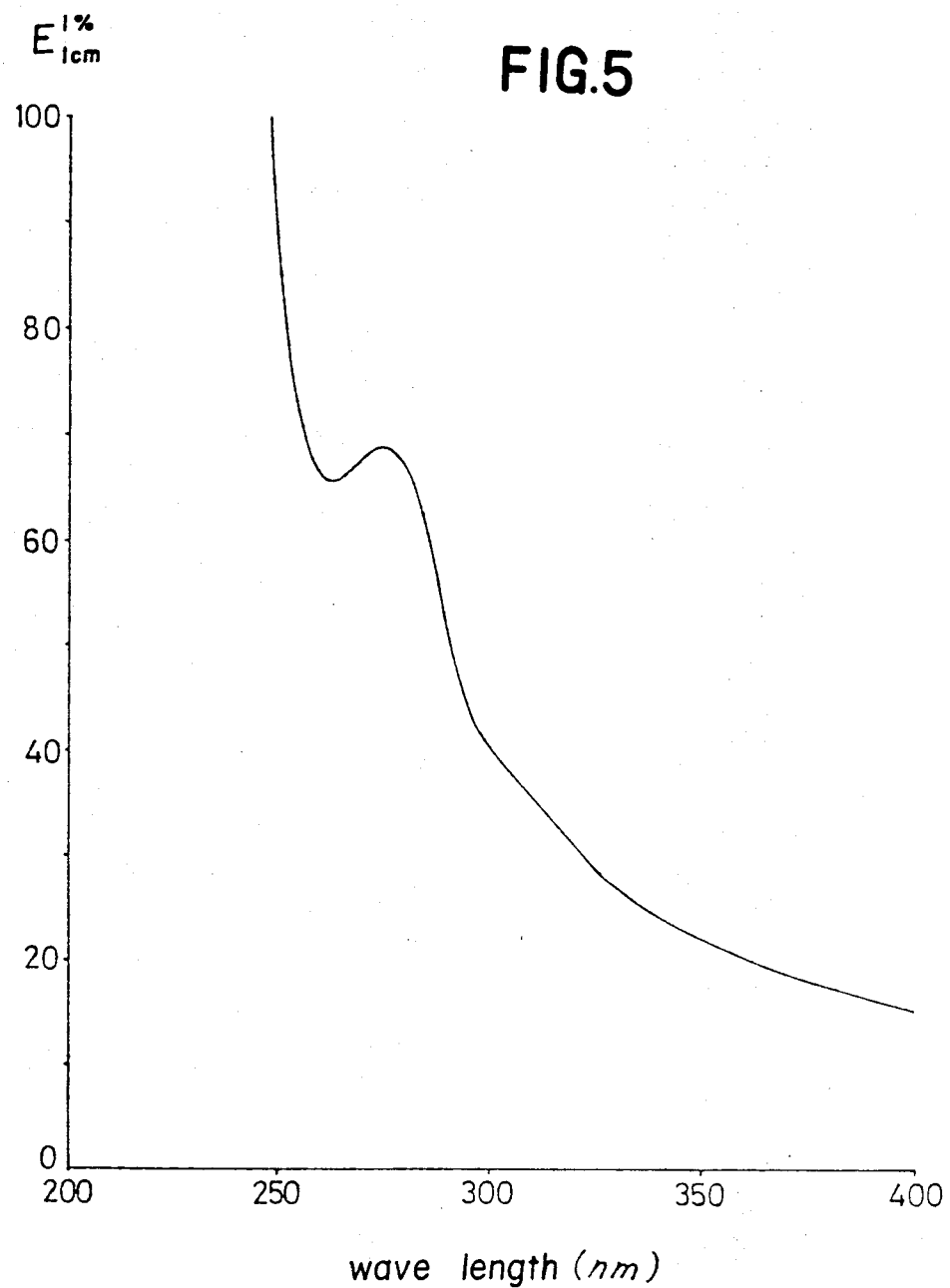

The invention will be described in greater detail in conjunction with the following examples, test examples and formulation examples.

EXAMPLE 1

To 10 g. of the dry neem bark was added 100 ml. of benzene. The mixture was allowed to stand for 1 hour with shaking at intervals to expedite extraction. The resulting mixture was filtered, and to the residue was added 100 ml. of benzene. The mixture was treated in the same way as above. The benzene extraction was repeated three times in total. The combined benzene extracts were concentrated to dryness to give powders. To the residue from the benzene extractions was added 100 ml. of methanol, and the mixture was subjected to the same procedures as described with benzene. To the residue from the methanol extraction was added 100 ml. of water (deionized) at room temperature, and the same procedures as above were repeated. To the residue from the water extraction was added additional 100 ml. of water, and the mixture was subjected to three extraction procedures in a boiling-water bath in the same manner as above. The hot-water extracts thus produced were concentrated on a rotary evaporator to dryness. There was obtained 270.5 mg. of dry powders of the hot-water fraction.

EXAMPLE 2

Extraction was carried out with 10 g. of the dry neem bark using procedures different from those in Example 1. The treatments were entirely the same as those in Example 1 except that no extraction with benzene was made, and ethanol was employed in place of the methanol. There was obtained 364.5 mg. of dry powders of the hot-water fraction.

Example 3

The same extraction treatments with water and hot water as those in the above examples were conducted with 10 g. of the neem bark. However, no extraction procedures using benzene and methanol or ethanol were employed. There was obtained 421.8 mg. of dry powders of the hot-water fraction.

Whereas the water employed in the above examples was deionized water, use of any water such as, for example, tap water, well water, distilled water, RO water (obtained using a reverse osmotic membrane) or the like produced similar results. Temperature of the water may be from 0° to 40° C. and is preferably room temperature. It is preferred to remove ingredients extractable with water as completely as possible.

The hot-water extracts of the neem bark produced as described in the above examples were tested for activities against sea urchin eggs, mouse L-5178Y cells, sarcoma 180 ascites and solid tumors. Pharmacological effects, doses and comparisons with known anti-cancer agents will be described below.

Test I

Antimitotic activity in sea urchin eggs using the neem extracts of the present invention were determined as follows:

Fertilized eggs of sea urchin, *Hemicentrotus pulcherrimus* or *Anthocidaris crassispina* numbered 200–300 together with 2 ml. of sea water were placed in a test tube. Immediately thereafter, 0.2 ml. of an aqueous or DMSO (dimethyl sulfoxide) solution of the test materials as obtained in the above examples was added to the test tube. Cell division of the fertilized eggs was then observed microscopically. Results are shown in Table I below. In the table, +++, ++, *, Δ and − represent complete inhibition of the egg division, about 50-80% inhibition of the egg division, one or two divisions of the eggs allowed, inhibition of the egg division after blastulation and no inhibition of the egg division, respectively.

TABLE I

| | | Effect on the cell division of sea urchin zyotes | | | |
|---|---|---|---|---|---|
| | | Concentration of the test solution (mg./ml.) | | | |
| Portion of neem | Fraction (Example No.) | 0.1 | 0.2 | 1.0 | 2.0 |
| Bark | water (1) | — | Δ | * | ++ |
| | water (2) | — | Δ | * | ++ |
| | hot water (1) | * | ++ | +++ | +++ |
| | hot water (2) | * | ++ | +++ | +++ |
| Leaves | water (2) | — | — | — | * |
| | hot water (2) | — | — | * | * |

It can be understood from the results of the above test in Table I that the hot water fractions have more potent activity than the water fractions and the fractions from the bark have more potent activity than those from the leaves.

Results of the tests as described above revealed that the neem extracts according to the invention inhibited not only the cell division but also fertilization of the sea urchin eggs. Those pharmacologically active ingredients which inhibit the fertilization and division of sea urchin eggs can find a wide range of applications as agrochemicals and pharmaceuticals. Effective dose level, formulation and toxicity considerations may be determined in accordance with the intended area of use.

Test II (Effects on mouse L-5178Y cells)

(1) Preparation of the cells

A medium containing $1 \times 10^5$ cells/ml. was prepared using mouse L-5178Y cells cultivated on RPMI-1640 medium containing 10% fetal bovine serum for 3 days. The medium was placed in a 96-well U-type microplate in an amount of 50 μl. per well.

(2) Method of evaluation

A portion of the test material, which was one of the extracts according to the invention described in the above examples, was dissolved in the medium to a final concentration in the medium as shown in Table II below. The amount of the solution per well was 50 μl. The test material thus prepared was incubated in a carbon-dioxide incubator at 37° C. for 2 days. After completion of the incubation, the cells were collected and counted well by well, and the cell counts were compared with cell count of control which contained no test material. The cell count of control was approximately $8.6 \times 10^5$/ml. In order to confirm the effects of the test materials, the same test was done with mitomycin C (MMC) or bleomycin (BLM). Results of the tests are shown in Table II below. In the table below, T/C represents the ratio of count of the cells treated with the test material to that with no test material added. $ID_{50}$ is the concentration of the test material required for decreasing concentration of the cells to ½ that of the control.

TABLE II

| | Effects on mouse L-5178Y cells | |
|---|---|---|
| Portion of neem | Fraction (Example No.) | $ID_{50}$ (μg./ml.) |
| Bark | Hot water (1) | 50 |
| | Hot water (2) | 58 |
| | Hot water (3) | 45 |
| | MMC | 0.09 |

TABLE II-continued

| | Effects on mouse L-5178Y cells | |
|---|---|---|
| Portion of neem | Fraction (Example No.) | $ID_{50}$ (μg./ml.) |
| | BLM | 7.8 |

(3) Results

There were produced test results as shown in Table II above with various hot-water fractions in the above examples and the agents for comparison. The hot-water extract fractions of the neem bark according to the present invention are so low in $ID_{50}$ value that the product in any of the examples evidently possesses a potent growth-inhibiting activity against the tumor cell, although the activity is below that of MMC or BLM. The activity would supposedly be increased if the hot-water fraction is purified for the active ingredient.

Test III (Effects on sarcoma 180 ascites tumor)

(1) Preparation of the test material

A portion of each of the extraction fractions was suspended or dissolved in 0.5% suspension of carboxymethylcellulose (CMC) in a phosphate buffer saline solution (PBS commercially available from GIBCO Laboratories, containing ca. 9.5 mM phosphate) to a predetermined concentration.

(2) Transplantation of sarcoma 180 tumor cells

Mouse sarcoma 180 tumor cells which have been subcultivated intraperitoneally in ICR mice were drawn from the mouse together with the ascites and diluted with physiological saline solution to a cell count of $10^8$ per ml. The tumor cell suspension thus prepared was transplanted by means of a syringe intraperitoneally into 4 week-old male ICR mice at a dose of 0.1 ml. Consequently, the cell count transplanted per mouse was $1 \times 10^7$.

(3) Administration of the test material

The test material as prepared above was intraperitoneally administered at a dose of 0.1 ml. per mouse for 4 days once a day from the next day of the transplantation of mouse sarcoma 180 tumor cells. A group of 6 mice was employed for each concentration of each test material. As active controls were used MMC, BLM, actinomycin D (ACD), 5-fluorouracil (5-Fu) and cyclophosphamide (CYP) to run similar tests. As a control was administered the CMC-containing PBS as described above only in the same way as above. The dose is expressed as weight per kg. bodyweight of mouse.

(4) Method of evaluation

On the 7th day of transplantation of the tumor cells bodyweight of each mouse was measured (X). Then, ascites was thoroughly drawn from the mouse, followed by measurement of the bodyweight (Y). X-Y is taken as the amount of ascites.

The drawn ascites was then introduced into a hematocrit tube and then centrifuged at 15,000 G for 5 minutes using a hematocrit rotor at a low temperature. There was thus made determination of the ascitocrit value, that is, proportion of the cells present in the ascites which corresponded to the hematocrit value in hematology. The value multiplied by volume of the ascites gives the volume of the cells present in the ascites. This is designated as total packed cell volume (TPCV). In case of the control, the total volume of ascites was 6-10 ml., and the TPCV was 1.6-2.5 ml.

Effect on the tumor was rated ineffective (−) when the TPCV ratio of the treated to the control (T/C) was 100–66%, plus 1 (+) when it was 65–41%, plus 2 (++) when it was 40–11%, and plus 3 (+++) when it was 10–0%. Test results for the materials from the hot-water extraction of the neem bark according to the present invention in comparison with the prior art materials are shown in Table III below.

TABLE III

| | Effects on sarcoma 180 ascites tumor | | | |
|---|---|---|---|---|
| Test material | Fraction (Example No.) | Dose (µg./kg.) | T/C (%) | Rating |
| Bark | Hot water (1) | 10 | 58.5 | + |
| | | 25 | 32.5 | ++ |
| | | 100 | 7.0 | +++ |
| | Hot water (2) | 25 | 28.4 | ++ |
| | | 100 | 5.3 | +++ |
| | Hot water (3) | 25 | 20.5 | ++ |
| Control | MMC | 0.5 | 0 | +++ |
| | | 1.5 | 0 | +++ |
| | BLM | 10 | 0 | +++ |
| | ACD | 0.1 | 0 | +++ |
| | 5-Fu | 20 | 0 | +++ |
| | CYP | 33 | 0 | +++ |

(5) Results

From the test results listed above it is evident that the hot-water extracts of the neem bark according to the invention possess high activities, although they are below those of MMC, BLM and other employed as controls. The minimum effective dose for the hot-water fraction (1) in the above table has been found from dose-T/C relationship to be approximately 6.5 mg/kg. As described in details below, the hot-water fraction of the present was somewhat toxic in mice at higher doses in the above-described tests. Although the neem bark extracts of the invention has not completely been purified, the activities are satisfactorily high as shown above. The activity would supposedly be increased if the material is further be purified.

Test IV (Effects on sarcoma 180 solid tumor)

(1) Preparation of the test material

Test materials were prepared in the same manner as in Test III under (1).

(2) Transplantation of sarcoma 180 solid tumor cells

A cell suspension containing $1 \times 10^8$ cells per ml. was prepared in the same way as in Test III under (2). Four week old-ICR mice was innoculated subcutaneously on the back with 0.1 ml. of the suspension by means of a syringe.

(3) Administration of the test material

As in Test III under (3), a group of 6 animals was used for each concentration of each test material.

(4) Method of evaluation

Grown tumor tissue was resected on the 15th21st days of the tumor cell transplantation and weighed. An average for the group of 6 animals was taken for the evaluation. The effect was evaluated on the basis of ratio of the average weight for the treated animals to that of the control animals (T/C). The average weight was 1.5–4.5 g. for the control animals. Ratios (T/C) of 100–71% were rated ineffective (−), of 70–51% plus 1 (+), of 50–21% plus 2 (++), and of 20–0% plus 3 (+++). Results with the test materials from the hot-water extracts of the neem bark according to the present invention and the prior art agents are shown in Table IV below.

TABLE IV

| | Effects on sarcoma 180 solid tumor | | | |
|---|---|---|---|---|
| Portion of neem | Fraction (Example No.) | Dose (mg./kg.) | T/C (%) | Rating |
| Bark | Hot water (1) | 10 | 91.2 | — |
| | | 25 | 76.7 | — |
| | | 100 | 40.0 | ++ |
| | Hot water (2) | 25 | 60.5 | + |
| | | 100 | 32.2 | ++ |
| | Hot water (3) | 25 | 54.8 | + |
| | MMC | 0.5 | 71.0 | — |
| | | 1.5 | 32.5 | ++ |
| | BLM | 10 | 43.5 | ++ |
| | ACD | 0.1 | 102.4 | — |
| | 5-Fu | 20 | 47.8 | + |
| | CYP | 33 | 0 | +++ |

Toxicity

The $LD_{50}$ value for the hot-water fraction of the neem bark as intraperitoneally administered in male ICR mice weighing 19–21.0 g. was 200 mg./kg. body-weight.

EXAMPLE 4

The 50 g. of the dry neem bark was added 500 ml. of water at 20° C. The mixture was allowed to stand at room temperature for about 24 hours for the extraction treatment. The resulting extraction mixture was filtered, and to the extraction residue was added 500 ml. of water at 20° C. The mixture was treated in the same way as above. The extraction procedures were repeated three times in total. To the residue from the extractions was added 500 ml. of water, followed by hot-water extraction by boiling the mixture over a gas burner for ca. 2 hours. The extraction mixture was then filtered to obtain an extract and an extraction residue. The hot-water extraction procedures were repeated three times in total. The combined extracts were concentrated to dryness to obtain 1418.0 mg. of powders. The powders thus obtained, 1000 mg., were dissolved in 200 ml. of water, and to the resulting aqueous solution was portionwise added absolute ethanol with stirring at room temperature to an ethanol concentration of 80% in the aqueous solution. After completion of the addition stirring was continued for an additional short period of time. Precipitates then formed were collected, washed with two portions of 80% ethanol, two portions of absolute ethanol and finally two portions of ether, and dried in vacuum to yield 671.3 mg. of a neem bark extract.

EXAMPLE 5

To 50 g. of the dry neem bark was added 500 ml. of methanol. The mixture was allowed to stand at room temperature for about 24 hours for the extraction treatment. The resulting extraction mixture was filtered, and to the extraction residue was added 500 ml. of methanol. The mixture was treated in the same way as above. The extracted procedures were repeated three times in total. The extraction residue thus obtained were treated in the same way as in Example 4. There were produced 1409.0 mg. of powders by subjecting the extraction residue to extraction treatments with water at 20° C., subsequently subjection the extraction residue to hot water extraction, and collecting and concentrating to dryness the resulting extracts. In 200 ml. of water was dissolved 1000 mg. of the powders, and to the resulting solution was added absolute alcohol. Precipitates then formed were collected to give 668.2 mg. of a neem bark extract.

EXAMPLE 6

The same procedures as in Example 5 were repeated except that the concentration to dryness of the hot-water extract employed therein was replacement by concentration of said extract to 300 ml. and subsequent addition of absolute ethanol to the concentrate. There was obtained 134.1 mg. of a neem bark extract.

EXAMPLE 7

The same procedures as in Example 5 were repeated except that ethanol was used as an extracting agent in place of the methanol to give 1371.8 mg. of a powdery hot-water extract. To a solution of 1000 mg. of the powders in 200 ml. of water was added absolute ethanol, and precipitates then formed were isolated to yield 654.8 mg. of a neem bark extract.

EXAMPLE 8

To 50 g. of the dry neem bark was added 500 ml. of benzene. The mixture was allowed to stand at room temperature for ca. 24 hours for extraction. The extraction mixture was filtered, and the residue from the extraction was treated in the same way as in Example 5. The treatment was to extract the extraction residue with methanol, subject the residue from the extraction to extraction with water at 20° C., subject the residue from the extraction to extraction with hot water and concentrate the extract thus obtained to dryness. There was yielded 1353.3 mg. of powders. To a solution of 1000 mg. of the powders in 200 ml. of water was added absolute ethanol, and precipitates then formed were isolated to yield 695.3 mg. of a neem bark extract.

EXAMPLE 9

The same procedures as in Example 5 were repeated except that absolute ethanol was added to an alcohol concentration of 50% in place of the alcohol concentration of 80% used therein. There was yielded 272.2 mg. of a neem extract.

EXAMPLE 10

The same procedures as in Example 5 were repeated except that absolute ethanol was added to an alcohol concentration of 25% in place of the alcohol concentration of 80% used therein. There was yielded 243.8 mg. of a neem bark extract.

The neem extracts produced in the above examples were tested for effects on sarcoma 180 ascites and solid tumors according to the methods described in the aforementioned Tests. Results are shown in Table V below.

TABLE V

Effects on transplanted sarcoma 180 tumors (mice)

| Test material | | mg./kg. | Ascites tumor T/C | Ascites tumor Rating | Solid tumor T/C | Solid tumor Rating |
|---|---|---|---|---|---|---|
| Example 5 | A* | 10 | 58.5 | + | 91.2 | — |
| | | 25 | 32.5 | ++ | 76.7 | — |
| | | 100 | 7.0 | +++ | 40.0 | ++ |
| | B** | 10 | 77.6 | — | 72.0 | — |
| | | 25 | 63.1 | + | 47.4 | ++ |
| | | 50 | 45.5 | + | 36.0 | ++ |
| | | 75 | 31.0 | ++ | 25.4 | ++ |
| Example 6 | B | 10 | 84.5 | — | 73.5 | ++ |
| | | 25 | 67.5 | — | 54.2 | — |
| | | 50 | 44.0 | + | 43.0 | + |
| | | 75 | 39.9 | ++ | 24.6 | ++ |
| Example 7 | A | 100 | 7.1 | ++ | 39.6 | +++ |

TABLE V-continued

Effects on transplanted sarcoma 180 tumors (mice)

| Test material | | mg./kg. | Ascites tumor T/C | Ascites tumor Rating | Solid tumor T/C | Solid tumor Rating |
|---|---|---|---|---|---|---|
| | B | 50 | 42.8 | + | 29.8 | ++ |
| Example 8 | A | 100 | 6.8 | +++ | 41.8 | ++ |
| | B | 10 | 79.2 | — | 73.3 | — |
| | | 25 | 61.0 | + | 49.4 | ++ |
| | | 50 | 44.8 | + | 38.1 | ++ |
| | | 75 | 33.7 | ++ | 23.0 | ++ |
| Example 9 | B | 50 | 55.8 | + | 68.0 | + |
| | | 100 | 41.2 | + | 49.2 | ++ |
| Example 10 | B | 50 | 47.6 | + | 69.2 | + |
| | | 100 | 40.1 | ++ | 58.3 | + |
| Mytomycin C | | 1.5 | 0 | +++ | 38.9 | ++ |

(Notes)
*The material indicated as A represents powders produced by concentrating the hot-water extract to dryness.
**The material indicated as B represents a product obtained by isolating precipitates formed by addition of an alcohol to the hot-water extract or by dissolving the material A mentioned above in water, adding an alcohol to the resulting aqueous solution and isolating precipitates then formed.

The minimum effective does for the not-water extracts of the neem bark according to the present invention in sarcoma 180 tumors was as shown in Table VI.

TABLE VI

Minimum effective dose for sarcoma 180 tumors (mg./kg. in mice)

| Test material | | Ascites tumor | Solid tumor |
|---|---|---|---|
| Example 5 | A | 6.5 | 30.0 |
| | B | 20.8 | 12.0 |
| Example 6 | B | 24.5 | 12.5 |
| Example 8 | B | 20.0 | 10.6 |

The results indicated above evidently show that the hot-water extracts of the neem bark according to the invention possess potent activities against sarcoma 180 tumors. Whereas the activity against the ascites tumor is reduced with the alcohol precipitates of the hot-water extracts as compared with the dried concentrates of the same, the activity against the solid tumor is much increased.

EXAMPLE 11

The 50 g. of the dry neem bark was added 500 ml. of water at 20° C. The mixture was allowed to stand at room temperature for about 24 hours for extraction. The extraction mixture thus obtained was filtered, and to the residue from the extraction was added 500 ml. of water. The mixture was treated in the same way as above. The extraction procedures were repeated three times in total. To the resulting extraction residue was added 500 ml. of water, followed by hot-water extraction by boiling the mixture over a gas burner for ca. 2 hours. The extraction mixture was then filtered to obtain an extract and an extraction residue. The hot-water extraction procedures were repeated three times in total. The combined extracts were concentrated on a rotary evaporator to dryness to obtain 1418.0 mg. of powders. A solution of 500.0 mg. of the powders thus obtained in 50 ml. of water was then placed in Spectra Por 6 (fraction molecular weight 50,000) for dialysis against water. Concentration of the internal dialysis solution to dryness on a rotary evaporator gave 317.6 mg. of a neem bark extract.

EXAMPLE 12

To 50 g. of the dry neem bark was added 500 ml. of methanol, and the mixture was allowed to stand at room temperature for about 24 hours for extraction. The extraction mixture was filtered. To the residue from the extraction was added 500 ml. of methanol, and the mixture was treated in the same way as above. The extraction procedures were repeated three times in total. The extraction residue thus obtained was treated in the same way as in Example 11. The treatment was to subject said extraction residue to extraction with water at 20° C., subject the extraction residue to extraction with hot water, collect and concentrate the extracts to dryness. There was obtained 1409.0 mg. of powders. A solution of 500.0 mg. of the powders in 50 ml. of water was treated with Spectra Por 6 (fraction molecular weight 50,000) to yield 322.7 mg. of a neem bark extract.

EXAMPLE 13

The same procedures as in Example 12 were repeated except that the hot-water extract was concentrated to 300 ml., and the concentrate thus obtained was treated with Spectra Por 6 (fraction molecular weight 50,000) in place of the concentration to dryness of the same used therein. There was yielded 341.0 mg. of a neem bark extract.

EXAMPLE 14 the same procedures as in Example 12 were repeated except that ethanol was employed in place of the methanol used therein as the extraction agent. There was obtained 1371.8 mg. of a powdery hot-water extract. A solution of 500.0 mg. of the powders thus obtained in 50 ml. of water was treated with Spectra Por 6 (fraction molecular weight 50,000) to yield 302.5 mg. of a neem bark extract.

EXAMPLE 15

To 50 g. of the dry neem bark was added 500 ml. of benzene, and the mixture was allowed to stand at room temperature for about 24 hours for extraction. The extraction residue thus obtained was treated in the same way as in Example 12. The treatment was to subject said extraction residue to extraction with methanol, subject the methanol extraction residue to extraction with water at 20° C., subject the water extraction residue to extraction with hot water and concentrate the hot-water extract to dryness. There was obtained 1353.3 mg. of powders. A solution of 500.0 mg. of the powders in 50 ml. of water was treated with Spectra Por 6 (fraction molecular weight 50,000) to yield 310.9 mg. of a neem bark extract.

EXAMPLE 16

The same procedures as in Example 12 were repeated except that Visking tube was used in place of the Spectra Por 6 used therein. There was yielded 370.9 mg. of a neem bark extract.

The neem extracts produced in the above examples were tested for effects on sarcoma 180 ascites and solid tumors according to the methods described in the aforementioned Tests. Results are shown in Table VII.

TABLE VII

| Effects on transplanted sarcoma 180 tumors (mice) | | | | | | |
|---|---|---|---|---|---|---|
| Test material | | Dose mg./kg. | Ascites tumor T/C | Rating | Solid tumor T/C | Rating |
| Example 12 | A* | 10 | 58.5 | + | 91.2 | — |
| | | 25 | 32.5 | ++ | 76.7 | — |
| | | 100 | 7.0 | +++ | 40.0 | ++ |
| | B** | 10 | 54.2 | + | 68.0 | + |
| | | 25 | 34.9 | ++ | 54.2 | + |
| | | 50 | 10.0 | +++ | 38.5 | ++ |
| | | 75 | 12.5 | +++ | 26.1 | ++ |
| Mytomycin C | | 1.5 | 0 | +++ | 38.9 | ++ |

(Notes)
*The material indicated as A represents powders obtained by concentrating the hot-water extract to dryness.
**The material indicated as B represents a hot-water extract of the neem bark by treating the material A above with a diaphragm.

The minimum effective dose for the neem bark extract produced in Example 12 against sarcoma 180 tumors was as shown in Table VIII.

TABLE VIII

| Minimum effective dose for sarcoma 180 tumors (mg./kg. in mice) | | | |
|---|---|---|---|
| Test material | | Ascites tumor | Solid tumor |
| Example 12 | A | 6.5 | 30.0 |
| | B | 6.7 | 10.3 |

The above results demonstrate that the hot-water extracts according to the present invention possess high activities against sarcoma 180 tumors. Especially noted is the much increased activity against the solid tumor the extract treated with a diaphragm as compared with the dried concentrate of te hot-water extract.

What we claim is:

1. Hot-water extract of neem bark which is characterized by being active against mouse L-5178Y cells and against transplanted sarcoma 180 tumors produced by successively contacting the bark of neem which is *Melia azadirachta* with a polar organic solvent selected from the group consisting of an alcohol, pyridine and acetone, and water at a temperature from 0° C. to 40° C. to form liquid extracts and a residue, subjecting said residue from said treatments to extraction with hot water at the boiling temperature to obtain hot-water liquid extract and purifying said hot water liquid extract by alcohol precipitation or dialysis using a diaphragm which fractionates molecules having a molecular weight of 50,000 or lower.

2. The hot-water extract of claim 1, wherein said purification is carried out by the alcohol precipitation using ethanol.

3. The hot-water extract of claim 2, wherein the alcohol precipitation is carried out using ethanol in an amount to provide an ethanol concentration of 80%.

4. The hot-water extract of claim 1, wherein said purification is carried out by dialysis using a diaphragm which is made of cellulose acetate or regenerated cellulose.

5. The hot-water extract of claim 1, wherein said polar organic solvent is an alochol selected from the group consisting of methanol, ethanol, propanol, and n-butanol.

6. The hot-water extract of claim 1, wherein said polar organic solvent is methanol.

7. The hot-water extract of claim 1, wherein said polar organic solvent is ethanol.

8. The hot-water extract of claim 2, wherein said polar organic solvent is methanol.

9. The hot-water extract of claim 3, wherein said polar organic solvent is methanol.

10. The hot-water extract of claim 4, wherein said polar organic solvent is methanol.

11. The hot-water extract of claim 2, wherein said polar organic solvent is ethanol.

12. The hot-water extract of claim 3, wherein said polar organic solvent is ethanol.

13. The hot-water extract of claim 4, wherein said polar organic solvent is ethanol.

14. Hot-water extract of neem bark which is characterized by being active against mouse L-5178Y cells and against transplanted sarcoma 180 tumors produced by successively contacting the bark of neem which is *Melia azadirachta* with a non-polar organic solvent selected from the group consisting of benzene, toluene, xylene, n-hexane, chloroform, carbon tetrachloride and ethyl acetate, with a polar organic solvent selected from the group consisting of an alcohol, pyridine and acetone, and with water at a temperature from 0° C. to 40° C. to form liquid extracts and a residue, subjecting said residue from said treatments to extraction with hot water at the boiling temperature to obtain a hot-water liquid extract and purifying said hot-water liquid extract by alcohol precipitation or dialysis using a diaphragm which fractionates molecules having a molecular weight of 50,000 or lower.

15. The hot-water extract of claim 14, wherein said non-polar organic solvent is benzene.

16. The hot-water extract of claim 14, wherein said polar organic solvent is an alcohol selected from the group consisting of methanol, ethanol, propanol, and n-butanol.

* * * * *